US005689334A

United States Patent [19]

Atkinson et al.

[11] Patent Number: 5,689,334

[45] Date of Patent: Nov. 18, 1997

[54] INTRACAVITY LASER SPECTROSCOPE FOR HIGH SENSITIVITY DETECTION OF CONTAMINANTS

[75] Inventors: George H. Atkinson, Tucson, Ariz.; Yehoshua Kalisky, Beer-Sheva, Israel; Jiamin Zhang, Painsboro, N.J.; Max F. Hineman, Boise, Id.; Esmail Mehdizadeh; Markus Wolperdinger, both of Tucson, Ariz.

[73] Assignee: Innovative Lasers Corporation, Tucson, Ariz.

[21] Appl. No.: 522,963

[22] Filed: Sep. 1, 1995

[51] Int. Cl.[6] .................... G01J 3/10; G01J 3/42; G01N 21/35

[52] U.S. Cl. .................... 356/326; 356/437; 250/339.13

[58] Field of Search .................... 356/300, 326, 356/432, 436, 437, 438, 439; 250/339.12, 339.13, 339.07

[56] References Cited

U.S. PATENT DOCUMENTS

| | | | |
|---|---|---|---|
| 4,648,094 | 3/1987 | McCollum et al. | 372/41 |
| 4,925,307 | 5/1990 | Cremers et al. | 356/318 |
| 4,951,287 | 8/1990 | Wyeth et al. | 372/32 |
| 4,987,575 | 1/1991 | Alfano et al. | 372/41 |
| 5,119,382 | 6/1992 | Kennedy et al. | 372/11 |
| 5,252,834 | 10/1993 | Lin | 250/458.1 |
| 5,257,085 | 10/1993 | Ulich et al. | 356/73 |
| 5,280,534 | 1/1994 | Gavrilovic et al. | 372/20 |
| 5,295,143 | 3/1994 | Rao et al. | 372/22 |

OTHER PUBLICATIONS

Atmanspacher et al, The American Physical Society, 32 (1), 1985, pp. 254–267.

Bohm et al, Optics Letters, vol. 18, No. 22, Nov. 15, 1993, pp. 1955–1957.

G.H. Atkinson et al, "Detection of free radicals by an intracavity dye laser technique," *Journal Of chemical Physics*, vol. 59, No. 1, pp. 350–354 (Jul. 1, 1973).

D.A. Gilmore et al, "Intracvity Absorption Spectroscopy with a Titanium: Sapphire Laser," *Optics Communications*, vol. 77, No. 5.6, pp. 385–398 (15 Jul. 1990).

G.H. Atkinson, "Intracavity Laser Spectroscopy," *Proceedings SPIE International Society of Optical Engineers*, vol. 1637, pp. 126–133 (1992); and.

D.A. Gilmore et al., "Intracavity laser spectroscopy in the 1.38–1.55 um spectral region using a multimode $Cr^{4+}$:YAG laser," *Optics Communications*, vol. 103, No. 5.6, pp. 370–74 (1 Dec. 1993);.

Purchase Orders: Number 7L–M0508, dated Nov. 15, 1995, and Nov. 29, 1995; and.

Quotation submitted to a potential customer, Sep. 2, 1994.

*Primary Examiner*—F. L. Evans
*Attorney, Agent, or Firm*—Benman Collins & Sawyer

[57] ABSTRACT

Contaminants are detected optically at concentrations below 1 part-per-million (ppm) and extending to a level approaching 1 part-per-trillion (ppt) by using intracavity laser spectroscopy (ILS) techniques. A solid-state laser with an ion-doped crystal medium contained in an optical resonator cavity (the ILS laser) is employed as a detector. A gas sample containing gaseous contaminant species is placed inside the optical resonator cavity and on one side of the ion-doped crystal. The output signal from the ILS laser is detected and analyzed to identify the gaseous species. The concentration of the gaseous species can be determined as well.

7 Claims, 10 Drawing Sheets

INTRACAVITY LASER SPECTROSCOPE FOR HIGH SENSITIVITY DETECTION OF CONTAMINANTS

TECHNICAL FIELD OF THE INVENTION

This invention relates, generally, to the detection of contaminants in gases, and more particularly, to the high sensitivity detection of gaseous molecules, atoms, radicals, and/or ions by laser techniques generally termed intracavity laser spectroscopy (ILS).

BACKGROUND OF THE INVENTION AND PRIOR ART

In the preparation of high quality semiconductor material (e.g. silicon films) for use in the microelectronics industry it is well known that contaminants must be controlled. Failure to control contaminants, as is also well known and appreciated, can result in the loss of significant resources as the resultant products are typically not useful for their intended purposes.

Generally, the starting materials in the fabrication of silicon films consist essentially of gases, typically denoted either "bulk" (e.g. nitrogen or argon) or "specialty" (e.g. hydrogen chloride, hydrogen bromide, boron trichloride). The successful operation of a fabrication facility designed to prepare semiconductor materials depends directly on the purity of the starting gases, as well as the gas handling capabilities available to preserve gas purity during the delivery of the gases to the process chamber and while material processing is taking place. Suitable control of the purity of such starting gases (i.e. monitoring and inhibiting high levels of contaminants as may be contained in the gases) is essential.

Under many current techniques, such control is achieved after the fact. That is, the silicon films so produced are periodically tested and the production line shut down only after such tests reveal the presence of high level contaminants. These processes, as will be appreciated by those skilled in the art, can lead to the waste of not only starting materials but also product which is produced prior to cessation of production. It is therefore desirable to monitor and control the contaminants as may be contained in such starting gases during production so as unacceptable contaminant levels are observed, production can be immediately, or at least shortly thereafter halted.

Many molecular, atomic, radical, and ionic species are present in the bulk and specialty gases used in the preparation (e.g. chemical vapor deposition or "CVD") and processing (doping and etching) of semiconductor materials that can be viewed as "contaminants." Such contaminants can degrade either the quality of the fabricated semiconductor material or the efficiency with which the semiconductor material is prepared. These contaminant species can interfere with the chemical process directly or even cause particles to be formed in the gas delivery lines or process chamber which subsequently deposit on the surface of the wafer material causing indirect performance defects.

The first step in controlling and/or eliminating these contaminants is their detection in the bulk and specialty gases used as starting materials. While this is generally recognized, heretofore practiced methods are generally inadequate. This is due, in large part to the situation created by seemingly ever increasing competitive industry standards which have developed. Specifically, as the size of microelectronic devices has decreased while performance specifications have been intensified, the requirements for gas purity (i.e., absence of microcontamination) has increased.

Against this backdrop it will likely be clear that several measurement criteria are important to detector effectiveness: (1) absolute detection sensitivity usually stated as parts-per-total number of gas molecules in the sample (e.g. parts-per-million or number of contaminant molecules per $10^{+6}$ background molecules); (2) species selectivity or the capability to measure the concentration of one species in the presence of other species; (3) rapidity of measurements to obtain a desired signal to noise ratio; (4) capability of monitoring contaminants in both non-reactive and reactive gases; and (5) linearity and dynamic range of gas concentrations that can be measured.

The current state-of-the-art devices for contaminant detection (e.g., water) encompass a variety of measurement techniques. For example, current state-of-the-art devices for water vapor detection utilize conductivity and electrochemical, direct absorption spectroscopy, and atmospheric pressure ionization mass spectroscopy (APIMS) measurement techniques. As discussed below, each of these methods falls to adequately address these requirements.

CONDUCTIVITY AND ELECTROCHEMICAL

Conductivity and electrochemical methods by solid-state devices exist which can detect water vapor at the 1–100 ppm range. Conductivity and electrochemical methods generally require direct physical contact between the sample and the device; thus, detection occurs after water molecules deposit on the solid-state surface. As a consequence, these devices do not perform well, if at all, with utilization of reactive or corrosive gases. Indeed, even their performance in non-reactive gases changes and/or deteriorates after even short exposures to reactive or corrosive gases. The linearity and dynamic range of response are usually limited to about one decade. The detection selectivity of these devices with respect to different gaseous species also is generally poor since the devices themselves will respond to a wide range of species without discrimination and selectivity is incorporated into the measurements only through whatever chemical selectivity, if any, is embodied in the coatings used to cover these devices.

DIRECT ABSORPTION

Direct absorption spectroscopy generally relates to the passing of light through the sample from an external source and measuring the reduction in light intensity caused by molecular, atomic, radical, and/or ionic absorption in the sample. Detection sensitivity depends directly on the subtraction of two large numbers (light intensity from the external source before it passes through the sample and its intensity after it exits the sample). This limits the detection sensitivity to the extent that direct absorption is generally considered a low sensitivity methodology.

APIMS

APIMS, initially used in the analysis of impurities in bulk nitrogen and argon and ambient air for air pollution studies, is now currently used by semiconductor manufacturers to detect trace levels of moisture and oxygen in inert bulk gases. With APIMS, the sampled gas is bombarded with electrons, or may be flame and photon excited, to produce a variety of ions that are then detected directly. Particularly, ionization occurs at atmospheric pressure in the presence of a reagent gas in the ionization source. APIMS typically exhibits detection sensitivities in the range of about 10 parts per trillion (ppt) in non-reactive gases. APIMS cannot even be used with reactive gas mixtures. Additional disadvantages of APIMS include $150,000–250,000 cost, extensive purging and calibration procedures, and the need for a knowledgeable operator.

In the context of the present invention, laser technology, specifically intracavity laser spectroscopy (ILS) is disclosed as being used as a detector (sensor) to detect gaseous species (contaminants) at very high sensitivity levels. While the methods and apparatus disclosed herein are particularly suited for application in fabrication of semiconductor components, it should be appreciated that the present invention in its broadest form is not so limited. Nevertheless, for convenience of reference and description of preferred exemplary embodiments, this application will be used as a benchmark. In connection with this application, laser technology offers distinct advantages to gaseous species (contaminant) detection over known methods and, particularly, to water vapor detection.

In conventional applications of lasers to the detection of gaseous species (contaminants), laser produced radiation is used to excite the gas sample external to the laser in order to produce a secondary signal (e.g. ionization or fluorescence). Alternatively, the intensity of the laser after it passes through a gas sample, normalized to its initial intensity, can be measured (i.e., absorption).

Intracavity laser spectroscopy (ILS) combines the advantages of conventional absorption spectroscopy with the high detection sensitivity normally associated with other laser techniques such as laser-induced fluorescence (LIF and multiphoton ionization (MPI) spectroscopy. ILS is based on the intracavity losses associated with absorption in gaseous species (e.g. atoms, molecules, radicals or ions) found within the optical resonator cavity of a multimode, homogeneously broadened laser. These intracavity absorption losses compete via the normal mode dynamics of a multimode laser with the gain generated in the laser medium. Traditionally, ILS research has been dominated by the use of dye lasers because their multimode properties fulfill the conditions required for effective mode competition and their wide tunability provides spectral access to many different gaseous species. Some ILS experiments have been performed with multimode, tunable solid-state laser media such as color centers and Ti:Sapphire. D. Gilmore, P. Cvijin, G. Atkinson, "Intracavity Absorption Spectroscopy With a Titanium: Sapphire Laser," *Optics Communications* 77 (1990) 385–89.

ILS has also been successfully used to detect both stable and transient species under experimental conditions where the need for high detection sensitivity had previously excluded absorption spectroscopy as a method of choice. For example, ILS has been utilized to examine gaseous samples in environments such as cryogenically cooled chambers, plasma discharges, photolytic and pyrolytic decompositions, and supersonic jet expansions. ILS has been further used to obtain quantitative absorption information (e.g. line strengths and collisional broadening coefficients) through the analysis of absorption lineshapes. Some of these are described in G. Atkinson, "Intracavity Laser Spectroscopy," SPIE Conf., *Soc. Opt, Eng.* 1637 (1992)

Some twenty years ago, another detection methodology was first explored in which the laser itself is used as a detector. G. Atkinson, A. Laufer, M. Kurylo, "Detection of Free Radicals by an Intracavity Dye Laser Technique," 59 *Journal of Chemical Physics,* Jul. 1, 1973. These methods, while suitable for use in laboratory settings are unacceptable for commercial settings. The constraints of commercial reality, as briefly noted above, essentially dictate that such a detector be conveniently sized, relatively inexpensive and reliable. Laboratory models fail to fully meet these requirements.

A laboratory demonstration of the feasibility of using ILS techniques for detecting small quantities of water vapor in a nitrogen atmosphere with a $Cr^{4+}$:YAG laser is described in D. Gilmore, P. Cvijin, G. Atkinson, "Intracavity Laser Spectroscopy in the 1.38–1.55 um Spectral Region Using a Multimode $Cr^{4+}$:YAG Laser," *Optics Communications* 103 (1993) 370–74. The experimental apparatus utilized was satisfactory for demonstration of operational characteristics, but undesirable for implementation in a commercial application as contemplated by the present invention.

In accordance with various aspects of the present invention, the present invention provides a user friendly, i.e. comparatively simple, detection system, having the advantages of direct absorption techniques but with dramatically increased detection sensitivities, capable of detecting gaseous species in reactive and non-reactive samples at a commercially viable cost, In this regard, the present invention addresses the long felt need for a method and apparatus for the high sensitivity detection of contaminants in reactive and non-reactive gas systems in commercial settings,

SUMMARY OF THE INVENTION

In accordance with various aspects of the present invention, contaminants are detected optically at concentrations below 1 part-per-million (ppm) and extending to level approaching 1 part-per-trillion (ppt) by using ILS techniques. A solid-state laser with an ion-doped crystal medium and operating in the 1300 nm to 1500 nm spectral region preferably serves as the detector. The gas sample containing gaseous contaminant species, for example water vapor, is placed inside the optical resonator cavity of the ion-doped laser (between reflective surfaces or mirrors) and on one side of the active medium. Laser media having $Cr^{4+}$:YAG and $Cr^{4+}$:LuAG are described here, but other ion-doped crystals having multiple longitudinal and transverse cavity modes can be used as well. For example, a Ti:Sapphire laser may be optically configured to provide ILS detection of oxygen and water vapor.

The ILS water vapor sensor system preferably comprises a pumping laser used to provide the optical excitement required to operate the ILS laser, a multimode ILS laser operated over the wavelength region in which the species of interest absorb, a gas sample cell placed within the optical resonator cavity of the ILS laser, a modulating device designed to periodically interrupt the intensity of the pumping laser beam and the output from the ILS laser, a wavelength dispersive spectrometer capable of spectrally resolving the output of the ILS laser, a detector capable of measuring the wavelength-resolved intensity of the ILS laser output, and an electronic circuit which can read the signal from the multichannel detector and convert it into electronic signal that can be processed by a computer.

BRIEF DESCRIPTION OF THE DRAWINGS

Preferred exemplary embodiments of the present invention will be hereinafter described in conjunction with the appended drawing figures, wherein like designations denote like elements, and:

FIG. 1A shows the basic configuration, while FIG. 1B shows that configuration as embodied in the preferred embodiment shown in FIG. 2;

DETAILED DESCRIPTION OF PREFERRED EXEMPLARY EMBODIMENTS OF THE PRESENT INVENTION

As previously briefly noted, the subject matter of the present invention is particularly well suited for use in connection with the manufacture of semiconductor components, and thus, a preferred exemplary embodiment of the present invention will be described in that context. It should be recognized, however, that such description is not intended as a limitation on the use or applicability of the subject invention, but rather is set forth to merely fully describe a preferred exemplary embodiment thereof.

In this regard, the present invention is particularly suited for detection of contaminants. Contaminants as used herein refers to molecular, atomic, radical and ionic species such as may be present in gaseous materials, such as in the gaseous materials which are used in the fabrication of silicon films, i.e. inlet lines. Alternatively, the term contaminant may also refer to the gaseous material itself, such as, for example when the detector of the present invention is used to determine if a line (e.g. HCI line) has been sufficiently purged of the gaseous material.

Figure 1A:
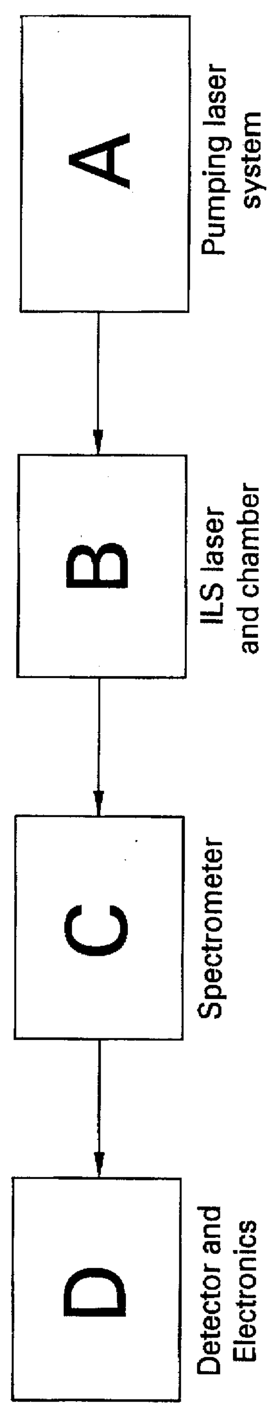
FIGS. 1A and 1B are schematic block diagrams of a contaminant detector system in accordance with the present invention.
Figure 1B:
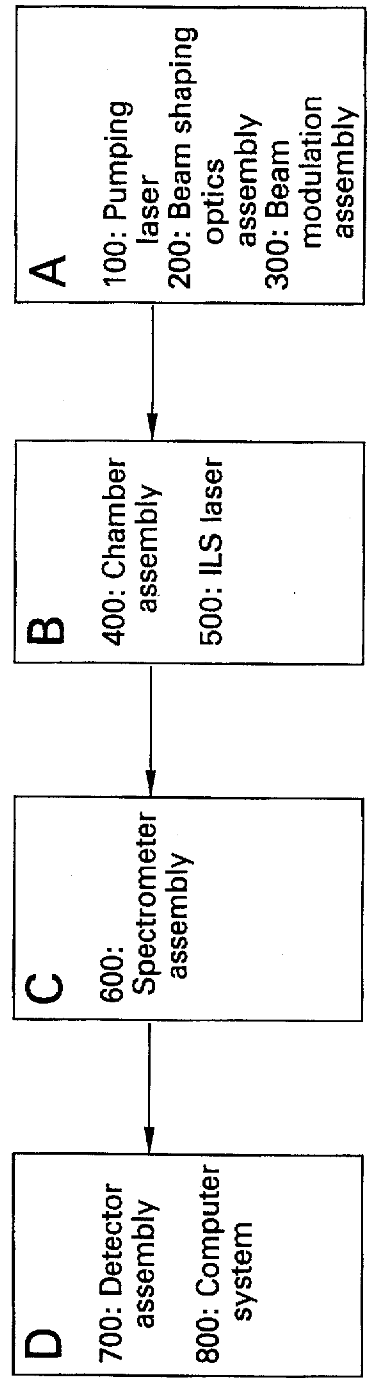

In accordance with a preferred embodiment of the present invention and with momentary reference to FIG. 1A, a gas (contaminant) detector system 10 suitably comprises a pumping laser system A, an ILS laser and associated chamber B, a spectrometer C and a detector with associated electronics (e.g. computer, etc.) D. More particularly, and with reference to FIGS. 1B and 2, pumping laser system A suitably comprises a pumping laser 100, a beam shaping optics assembly 200 and a beam modulation assembly 300; laser and chamber B suitably comprises a chamber assembly 400 and an ILS laser 500; spectrometer C suitably comprises a spectrometer assembly 600; and, detector D suitably comprises a detector assembly 700 and a computer system 800. As will be described more fully herein, gas detector system 10 advantageously detects gaseous species (contaminants) which are suitably contained in a gas sample. In general, pumping laser driver system A suitably pumps ILS laser B, preferably at or near the threshold level such that a laser beam passes through the gas sample such that the spectrum of the gas sample may be obtained. This spectrum is suitably detected through use of detector/computer system D which, upon manipulation, enables the reliable and accurate determination of the presence and concentration at high sensitivity levels of gaseous species (contaminants) which may be contained within the gas sample.

With reference to FIG. 10, and in order to more fully explain the scientific principles utilized in accordance with a preferred embodiment of the present invention, the general principles of intracavity laser spectroscopy (ILS) are illustratively shown. As is known, in its simplest terms, a laser can be described as containing a gain medium, in which optical gain is produced, and a resonator, comprised of optical elements such as mirrors. Optical losses may appear in both the medium and the optical elements comprising the laser cavity (e.g. the resonator). With particular reference to FIG. 10A, a laser device in its simplest form can be schematically illustrated as including a gain medium 1A around which respective mirrors 2A and 3A are placed. Mirrors 2A and 3A are typically coated to have high reflectivity surfaces over a broad spectral range. For example, the mirror coating on mirror 2A may be totally reflective, while the mirror coating on mirror 3A may be partially reflective thereby permitting some light to escape from the laser cavity. The spatial region between the reflective surfaces of mirrors 2A and 3A in which the gain medium is placed defines the laser resonator or cavity, and in the context of the present invention relates to the so-called "intracavity region."

The intensity (I) of the laser output may be determined both by the wavelength region over which the gain medium operates ($\lambda$) and the reflectivity of the resonator elements (e.g. mirrors 2A and 3A). Normally this output is broad and without sharp, distinctive spectral features, as is shown in the plot of I versus wavelength ($\lambda$) provided in FIG. 10D of FIG. 10.

Figure 10D:
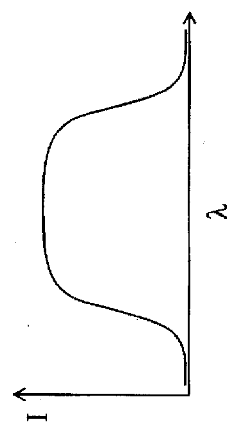
FIGS. 10D–10F are graphs which represent the accompanying graphical spectral outputs (intensity versus wavelength) obtainable from the devices depicted in FIGS. 10A–10C, respectively.
Figure 10E:
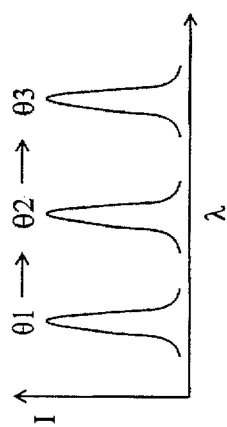
Figure 10F:
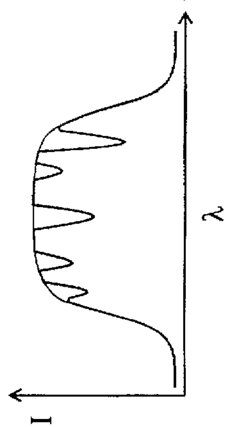
Figure 10A:
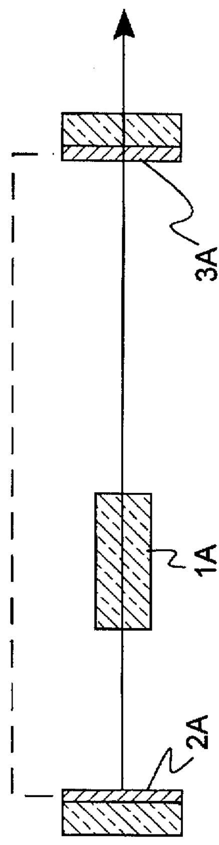
FIG. 10A–10C includes schematic representations of simple laser devices.
Figure 10B:
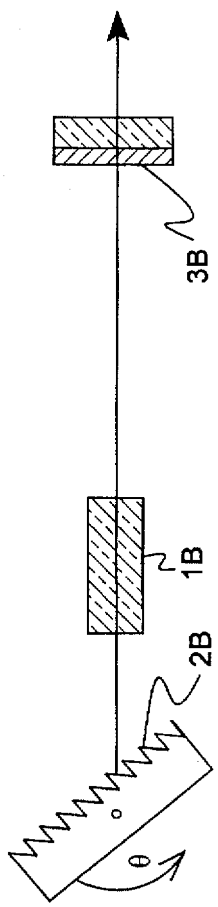

By selecting different optical elements to form the laser cavity, the spectral output of the laser can be altered or "tuned." For example, and with continued reference to FIG. 10 and in particular schematic representation 10B thereof, a tuned resonator cavity may include a diffraction grating 2B which replaces the highly reflective mirror 2A shown in FIG. 10A. As shown, the laser device therefore includes diffraction grating 2B, mirror 3B and a medium 1B positioned therebetween. In general, the result in spectral output from this tuned laser will be narrowed and appear as wavelengths within the original spectral output of the laser defined by the gained medium and the mirrors (FIG. 10A). For example, a schematic plot of intensity (I) versus wavelength ($\lambda$) illustrating a narrowed output is depicted in FIG. 10E.

Figure 10C:
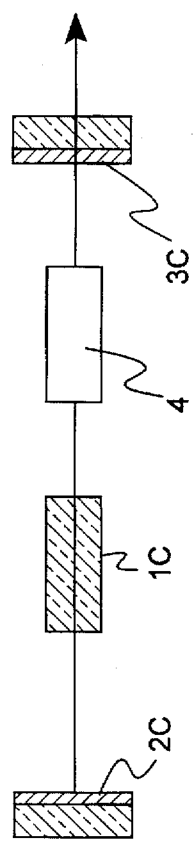

The laser output can also be altered by placing gaseous molecules, atoms, radicals and/or ions in either their ground or excited states inside the optical resonator (e.g. cavity). With reference to FIG. 10C, a laser so configured may include a highly reflective mirror 2C, a partially reflective mirror 36 with a medium 1C and an intracavity absorber 4 placed therebetween. In this case, intracavity absorber 4 may comprise such gaseous species (e.g. the sample containing contaminants). The effect of the intracavity gaseous species on the laser output can be observed. For example, a plot of I versus λ for such a device is shown in FIG. 10F. FIG. 10F comprises an absorption spectrum of the gaseous species contained within intracavity absorber 4. The distinct absorption features illustrated in FIG. 10F arise from the intracavity species losses against which the laser gain must compete. Thus, the absorption spectrum of the intracavity species may appear in the spectral output of the laser. In particular, the laser output intensity (I) at wavelengths where the stronger intracavity absorption features compete effectively against the gain properties of the resonator are more reduced. As a result, as illustrated, instead of a relatively smooth continuous output, such as shown in FIG. 10D, a structured laser output such as shown in FIG. 10F may be observed. The decreases in intensity (I), as shown in FIG. 10F, are due to absorption by the gaseous intracavity species, i.e. the more intense the absorption features, the larger the decrease in the laser output intensity. In accordance with the present invention, the absorption spectrum obtained by intracavity laser measurements in which an intracavity absorber is employed can be utilized for the high sensitivity detection of such gaseous species. It has been found that each gaseous species can be uniquely identified by its respective absorption spectrum (signature) and thus can be used to confidently identify such gaseous species (contaminant).

The present inventors have found that the appearance of the absorbing species (gaseous elements) within the laser resonator before and/or during the competition between gain and losses which naturally occur as the laser system approaches threshold give rise to enhanced detection sensitivity through use of ILS. In view of the fact that the losses associated with the intracavity absorber become part of the competition between the gain and losses within the laser, even a small absorbance associated either with a weak absorption transition and/or an extremely small absorber concentration is amplified dramatically during the gain/loss competition. As a result, such competition clearly appears in the output of the ILS signal (see FIG. 10F). Thus, using these principles, ILS can be utilized to detect both weak absorption and/or extremely small absorber concentrations.

Figure 2:
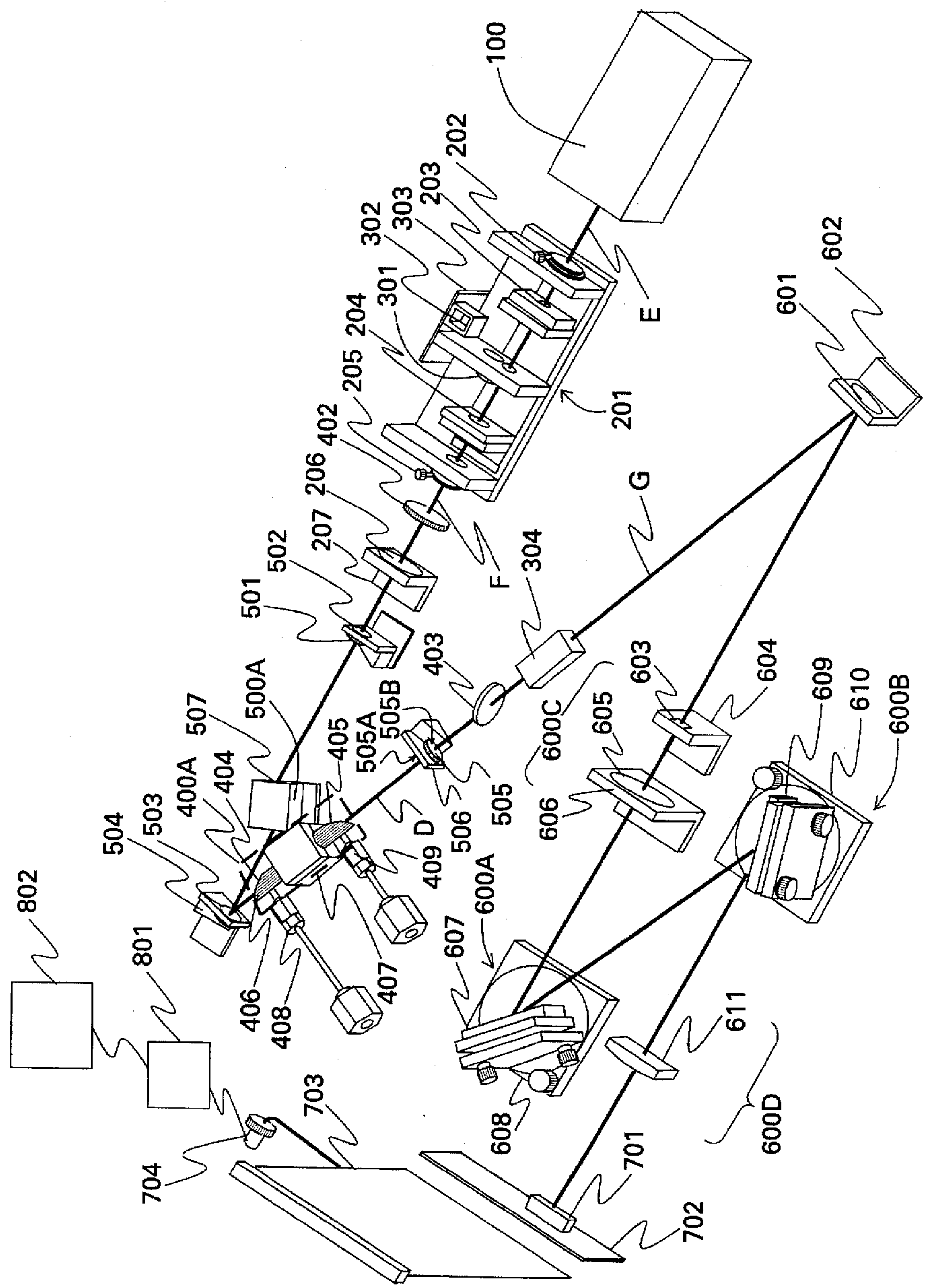
FIG. 2 is a more detailed schematic perspective view of a preferred embodiment of a contaminant detector system in accordance with the present invention.

Against the backdrop of these general principles, in the context of the present invention, the present inventors have devised a commercially viable contaminant sensor system 10 which provides enhanced detection of contaminants in gaseous samples. With reference now to FIGS. 1A and 2, and in accordance with a preferred exemplary embodiment of the present invention, a detection system 10 suitably includes laser driver 100, an ILS chamber assembly 400 in which ILS laser 500 is contained. Spectrometer 600 and a detector/computer system 700,800 are suitably optically connected to the output from laser 500 whereat the absorption spectrum is suitably manipulated thus enabling the high sensitivity detection of the presence and/or concentration of gaseous species (contaminants).

In order to drive ILS laser 500, system 10 requires a pumping source which delivers radiation of sufficient power and within a suitable wavelength region so as to optically excite ILS laser 500 at or slightly above its threshold. In this regard, it is important that ILS laser 500 operate such that the gain in the laser medium exceeds the overall optical losses, including those associated with the gain medium, mirrors, and non-mirror intracavity optical elements, as well as the absorption of any gaseous species within the optical resonator cavity. Moreover, preferably laser 500 operates with multiple longitudinal modes, i.e. over a broad wavelength region. Typically, a desirable bandwidth over which laser action occurs is between about 2 nm and about 15 nm. While ILS laser 500 can also operate with more than one transverse resonator mode, such is not necessary. Thus, in accordance with a preferred exemplary embodiment of the present invention, the laser driver comprises an optical pumping laser 100. Suitably, the optical parameters (e.g. average power density, peak power density, divergence and beam diameter) of pumping laser 100 advantageously match the optical requirements of ILS laser 500. As will be appreciated, to do so it is necessary to determine how many photons can be delivered within a specific volume and at a given distance from the pumping laser over a particular period of time. In general, in accordance with the present invention, such determinations are made in accordance with known theoretical and quantitative equations such that the pumping laser is suitably selected to advantageously match the optical characteristics of ILS laser 500.

While other drivers may be utilized in the context of the present invention, preferably, a pumping laser is selected on the basis of its operational wavelength and on its optical parameters in a manner such that it can alone be used to excite ILS laser 500. As will be described in greater detail hereinbelow, in cases where pumping laser 100 is not effective alone to drive (e.g. pump) ILS laser 500, beam modification optics, such as beam shaping assembly 200, can be utilized. However, in those cases where the radiation emanating from laser 100 suitably matches the mode volume of the ILS gain medium contained within ILS laser 500, such beam modification optics are unnecessary.

In accordance with a particularly preferred aspect of the present invention, pumping laser 100 suitably comprises a laser operating at approximately a 1064 nm wavelength, having an output power greater than about 2.8 watts with a $TEM_{00}$ transverse mode structure. Suitably, a beam E propagating from pumping laser 100 has a linear polarization and is rotatable perpendicular to the plane of propagation. Preferably, the divergence of the output beam (beam E) from pumping laser 100 is on the order of less than 0.5 mrad and evidences a beam diameter on the order of less than 5 mm. A particularly preferred pumping laser is model T20-1054C from Spectra Physics of Mountain View, Calif. As will be explained more fully hereinbelow, use of such a pump laser 100 typically requires use of beam shaping optics assembly 200.

It should be appreciated that driver 100 may comprise any suitable optical pumping source, either coherent or incoherent, continuous or pulsed, that will suitably excite ILS laser 500. As a result, even in accordance with the previously recited preferred embodiment, pumping source 100 operates in a conventional manner and emits radiation over a desired frequency band and having a desired bandwidth.

With continued reference to FIG. 2, ILS laser 500, in the simplest case comprises an optical resonator cavity defined by the entire optical path length between respective mirrors 501,503,505. In those cases where system 10 is used to detect gases (contaminants) within the sample which do not chemically react with the components of the laser itself (e.g. gain medium or crystal, mirrors, mechanical mounting and the like), the resonator cavity can be defined by the region between mirrors 501,503, and 505. In such a case, the gas sample region comprises the region between mirrors 501, 503,505 (excluding the laser crystal 507).

However, for samples which do chemically react (e.g. a corrosive gas) with one or more of the laser components, it is desirable to separate the gas sample region from such components. In accordance with a preferred embodiment of the present invention, a separate sample system 400A may be advantageously utilized to isolate the sample from the laser components.

Figure 3:
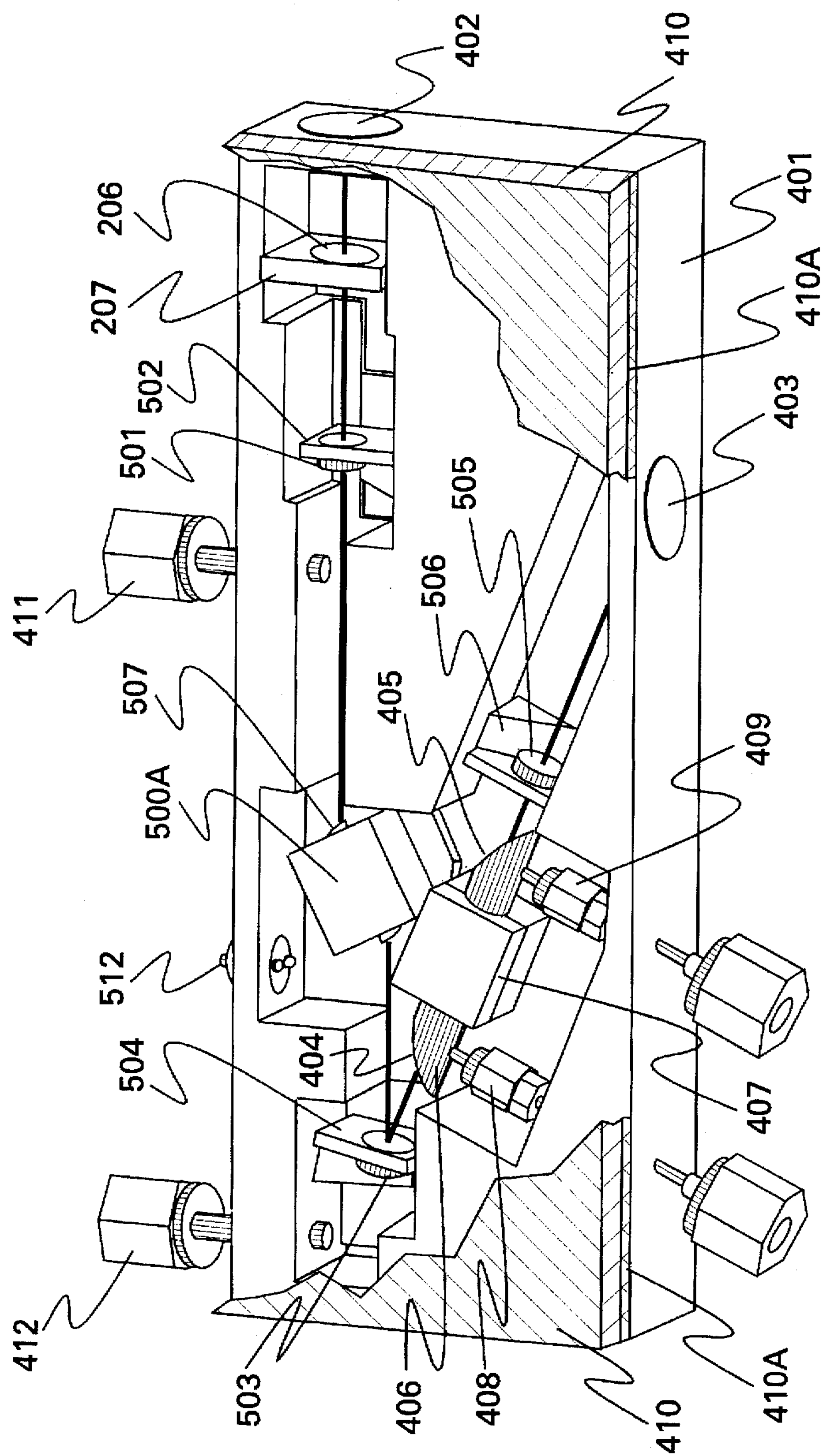
FIG. 3 is a schematic perspective view of an ILS chamber including the chamber components depicted in FIG. 2, some of the components shown in partially broken away fashion.

With reference to FIGS. 2 and 3, in accordance with this preferred aspect of the present invention, sample system 400A preferably comprises a gas sample cell body 406 suitably maintained within a gas sample cell holder 407. Respective cell windows 404 and 405 are suitably mounted on the distal ends of gas sample cell body 406 and provide optical access to the sample within cell body 406. Windows 404 and 405 also suitably seal cell body 406. As will be discussed in greater detail below, the region in which system 400A is suitably placed is astigmatically compensated. Given this astigmatic compensation, windows 404 and 405 do not have large effects on the ILS laser beam except with respect to transmission. An inlet conduit 408 and an outlet conduit 409 are operatively connected to gas cell body 406. With reference to FIG. 3, couplings 408 and 409 are advantageously employed to ensure efficient and effective passage of a gas sample into and out of gas (contaminant) sample cell system 404–409.

Suitably, cell body 406 comprises a stainless steel body having dimensions suitably on the range of 10 millimeters (mm) to 90 mm. In accordance with a particularly preferred aspect of the present invention, sample system 400A defines an opening (i.e. the opening in body 406) having a diameter on the order of about one-eighth of an inch; preferably the opening in body 406 is symmetrically in the center of gas sample cell body 406. Preferably, the diameter of the opening in cell body 406 is suitably selected to be significantly larger than the diameter of the incoming beam such that optical alignment of gas sample system 400A may be easily obtained. Windows 404, 405 may be formed an optically compatible material, such as Infrasil™ available from Research Electro Optics of Boulder, Colo.

In accordance with a preferred aspect of the present invention, the thickness of windows 404, 405 is suitably selected to avoid interferometric effects which may interfere with the quality of the ILS absorption spectrum obtained through operation of detector 10. In accordance with this aspect, the material used in forming windows 404, 405 is optimally chosen to minimize absorption losses in the region over which ILS laser 500 operates, such as in the range of 1350 nm to 1550 nm. Windows 404, 405 are suitably oriented at Brewster's angle so as to further minimize reflective losses from the window surfaces.

As so configured, gas sample cell 404–406 suitably permits beam F to pass through a gaseous sample to be analyzed. Couplers 408, 409, are suitably selected to provide easy adjustment such as may be required to realign and/or align windows 404, 405 within ILS laser 500 without significantly altering the threshold pumping conditions. The resonator cavity in the case where system 400A is employed is suitably defined by the physical length between mirrors 501,503,505 (including the laser crystal 507 and including the region between windows 404,405 as well as windows 404 and 405 themselves that comprise the sample system 400A). However, in such cases where the sample does not chemically react with the laser components, the sample cell may nominally be defined by the physical region between mirrors 501,503,505 (excluding laser crystal 507).

In the event that system 400A is present within chamber 400, it is necessary that any gases (contaminants) within chamber 400 that are to be detected are suitably removed or eliminated such that the absorption spectrum of the sample obtained through use of device 10 is accurate as to the amount or presence of those gases (contaminants) within the gas sample contained within system 400A. In accordance with a preferred aspect of the present invention, chamber 400 advantageously evidences a sealed container which can be either purged of gas(es) (contaminant(s)) to be detected, or evacuated to remove gas(es) (contaminant(s)) to be detected, or in which the level of gas(es) (contaminant(s)) can otherwise be reduced below the level to be detected in the sample system 400A.

Referring to FIGS. 2 and 3, in accordance with a preferred embodiment of the present invention, ILS chamber 400 (excluding the sample system 400A) suitably comprises a container base 401 and attachable top 410. Respective windows 402,403 are suitably positioned in the walls of body 401 in a suitable manner and position relative to the optical resonator cavity defined therewithin. Container base 401 and top 410 suitably comprise stainless steel or aluminum. Top 410 is advantageously secured to body 401 in accordance with any conventional technique suitable to permit evacuation, purging and/or further removal of contaminants therewithin. For example, a gasket 410A or other suitable means together with sealing devices (e.g. mechanical assists, adhesives and the like all not shown ) may be employed for such purposes.

Windows 402,403 are suitably disposed in the walls of container 401, thereby providing optical access to ILS chamber 400. Preferably windows 402,403 comprise optical windows with such as those available as models P910125 and P117125 from ESCO of Oak Ridge, N.J. Preferably, window 402 is suitably provided with an antireflective (AR) coating on the order of about 1000 nanometers (nm) about 1100 nm, and optimally about 1064 nm. On the other hand, window 403 preferably comprises an optical window without an AR coating. Window 402 is suitably designed to provide for maximum transmission at 1064 nm. Similarly window 403 is suitably designed to provide maximum transmission over the operational wavelength region of the ILS laser 500 (e.g. 1350 nm to about 1550 nm).

In such cases where the contaminant comprises water vapor, it is necessary that water levels in chamber 400 be reduced below those which are contained within the sample. In accordance with the present invention, detection levels of up to 10 parts per trillion (ppt) are obtainable. While any now known or hereafter devised method for removing contaminants (for example water) from chamber 400 (excluding the sample system 400A) can be practiced within the context of the present invention, preferably, chamber 400 is appropriately sealed and inert gases, such as nitrogen are pumped therein. In some instances it may be necessary to further evacuate the chamber so as to create a vacuum which removes substantially all contaminants contained therein. In accordance with yet a further aspect of the present invention, a getter (not shown) may be advantageously employed with chamber 400 to provide even further elimination of water within chamber 400. As will be appreciated by those skilled in the art, a getter (e.g. a molecular sponge) having the capacity for continuously absorbing water may be utilized to reduce the level of water (contaminants) below the water concentration that is to be detected in the gas sample cell 404–406 (e,g., 10 ppt). A particularly useful getter comprises model PS3N13N1 available from the Pall Corporation of City of Industry, Calif.

As briefly mentioned above, ILS sensor 500 suitably optically detects gaseous species (contaminants, e.g., water vapor) contained in a sample placed within chamber 400. In accordance with the present invention, ILS laser 500 suitably comprises a crystal 507 mounted in a crystal holder 508. Crystal 507 is suitably mounted in crystal holder 508 such that crystal 507 also is optimally placed with reference to the incoming beam. As previously briefly mentioned, the incoming beam is suitably shaped either by operation of pump 100 or through use of beam shaping assembly 200 such that incoming beam D suitably matches the mode volume of the ILS gain medium (e.g. crystal 507). In general, ILS laser 500 is suitably configured such that the laser beam in the intracavity region is substantially parallel (i.e., astigmatically compensated) in the region where the beam is directed to gas sample, e.g. as contained within system 400A. While a variety of optical configurations may be employed for this purpose, these mirror configurations have been found to be particularly advantageous. Such a configuration permits the accurate astigmatic compensation of the incoming beam thus permitting simultaneous meeting of the optical conditions necessary to pump ILS laser at the lasing threshold and generation of a laser beam which is substantially parallel as it is directed to the gas sample, such as contained within system 400A.

In accordance with this aspect of the present invention, respective mirrors 501,505 and a folding mirror 503 are suitably employed for this purpose. Mirror 501 preferably comprises an optical mirror having an AR coating between about 1000 nm and 1100 nm, optimally 1064 nm. Mirror 501 has a coating that effectively provides on the order of about 99.8% to about 100% reflectivity in the desired spectral region (e.g. about 1350 to about 1550 nm). Suitably, mirror 501 evidences a radius of curvature (ROC) of about 10 centimeters and evidences a diameter on the order of about 1.0 to about 1.30 cm, optimally about 1.27 cm. Preferably, mirror 501 comprises a mirror available from Rocky Mountain Instrument Co. of Longmont, Colo.

Preferably, mirror 503 comprises a folding mirror which is configured similarly to mirror 501. In accordance with a preferred aspect of the present invention, mirror 503 has a coating suitable to achieve reflectivity of about 99.8% to about 100% over the desired spectral region (e.g. about 1350 nm to about 1550 nm). Mirror 503 suitably evidences a diameter on the order of about 1.0 to about 1.3 cm, optimally about 1.27 cm.

Preferably, mirror 505 comprises a flat mirror (ROC≈∞). With reference to FIG. 2, side 505A of mirror 505 facing mirror 503 is advantageously provided with a reflective coating between 1350 nm and about 1550 nm. The other side 505B of mirror 505 is suitably uncoated. Preferably surfaces 505A and 505B ate suitably wedged one against the other at an angle of on the order of about 0.5 to about 3.0 degrees, optimally about 1.0 degree. The present inventors have found that wedging such surfaces in this manner tend to minimize undesirable reflections which may lead to interference effects.

Mirrors 501,503,and 505 are suitably mounted in respective mirror mounts 502, 504, and 506. While any mount which is configured to maintain the mirror in place may be utilized, suitable mounts include NEW FOCUS 9800 series mounts which are available from Newport/New Focus of Sunnyvale, Calif.; high vacuum compatible mounts NEW FOCUS model 9581 are particularly preferred. Mounts 502, 504, and 506 also enable mechanical adjustment to optically align the ILS cavity within chamber 400. For example, the present inventors have found that the efficiency of the ILS laser 500 is optimized for a laser configuration in which mirrors 501 and 505 are aligned for a beam incident angle of about 0° and mirror 503 is aligned for a beam incident angle of about 12.5°. Through the appropriate design, placement and configuration of mirrors 501,503 and 505 beam D is substantially parallel (i.e. collimated) in the region between mirrors 503 and 505. As a result, sample system 400A can be inserted within the intracavity region without significant deleterious effect in the performance of ILS laser 500. While certain tolerances are of course permitted in the design and arrangement of mirrors 501,503 and 505, without astigmatic compensation, ILS laser 500 may become misaligned or operate in an uncontrolled fashion.

ILS laser crystal 507 preferably operates in a wavelength region suitable for detection of the contaminants contained within the gas sample (e.g. water vapor) over which a signature absorption spectrum can be obtained. As previously mentioned, laser crystal 507 generally exhibits the properties of a multimode laser system. Light produced by laser crystal 507 typically has a mode spacing of about 450 megahertz (MHz) to about 550 MHz, preferably about 500 MHz, thus ensuring accurate spectral replication of absorption bands. While any crystal may be utilized in the context of the present invention, a $Cr^{+4}$:YAG or $Cr^{+4}$:lutetium (Lu)AG laser crystal may be optimally used in connection with the present invention. Moreover, other hosts for the $Cr^{+4}$ ions may be used and other doped ions into these host crystals may be substituted. The present inventors have found that the low gain efficiency of a $Cr^{+4}$ system in a garnet host (e.g. YAG or LuAG) can be operated successfully as a laser using a crystal that is on the order of about 10 mm to about 30 mm in length and 5 mm in diameter. Preferably the doped concentration is in the range of about 0.10% to about 0.30% in such garnet host. A particularly preferred laser medium comprises a $Cr^{+4}$:YAG or $Cr^{+4}$:LuAG crystal cut at Brewster's angle to minimize reflective losses. More particularly a $Cr^{+4}$:YAG crystal cut at Brewster's angle (e.g. for a crystal refractive index where n is about 1.82 and $\Theta_B$ is about 61.20) having a crystal length of about 23 to about 27 mm at about a 0.15% dopant level has been found to be particularly advantageous in the context of detector 10 in accordance with the present invention.

Laser crystals currently available, while improving in efficiency, have considerable losses associated with them. The losses translate to heat. In accordance with the present invention crystal 507 suitably is mounted in a manner allowing for the effective removal of the heat thus generated in operation. It should be appreciated, however, that as the efficiency of laser crystals continue to improve as new crystals are developed, the need or requirements on heat removing devices will be reduced and likely, at some point, the losses will be small enough that the need to remove the heat may be eliminated all together. However, using crystals presently available and in accordance with various aspects of the present invention, ILS laser system 500 preferably further comprises a heat sink system 500A.

Figure 5:
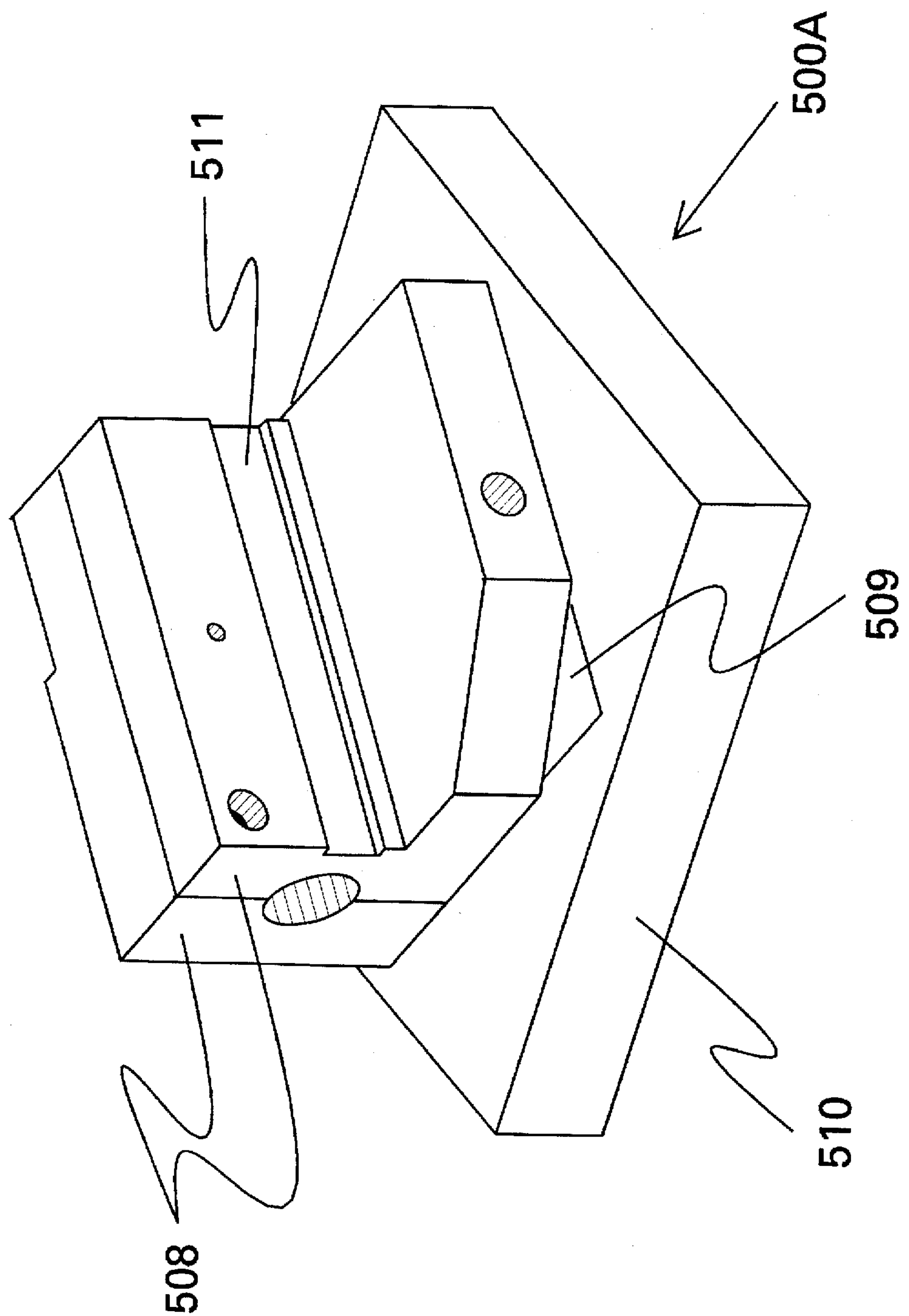
FIG. 5 is a perspective view of an exemplary ILS laser crystal holder and heat sink useful in connection with the contaminant detector system shown in FIG. 2.

With continued reference to FIG. 2 and additional reference to FIG. 5, heat sink system 500A desirably is operatively connected to mount 508 and crystal 507 (not shown in FIG. 5). As shown best in FIG. 5, holder 508 preferably comprises a two-part holder 508 suitably arranged to snugly maintain crystal 507 in an operative arrangement. Heat sink system 500A preferably comprises a copper heat sink bridge 510, a thermal electric cooler 509 and a thermal electric sensor 511. Bridge 510 preferably comprises oxygen-free copper. Thermal electric cooler 509 preferably comprises model CP1.0-71-05L available from Melcore of Trenton, N.J. Thermal electric sensor 511 preferably comprises an Omega type 100W 30 Platinum (RTO) resistant temperature detector. Mount 508 together with bridge 510, cooler 509 and sensor 511 serve to properly align crystal 507 with respect to the other optical elements comprising ILS laser 500, as well as enable control of the thermal properties of the crystal.

In accordance with the preferred aspect of the present invention, heat sink system 500A is in direct physical contact with crystal 507. Heat produced by normal operation of crystal 507 through optical excitation occasioned by beam E is effectively conducted away from crystal 507 thereby maintaining a relatively constant operating crystal temperature. Preferably, crystal holder 508 comprises copper/aluminum which is operatively connected to cooler 509 and heat sink bridge 510. Suitably, heat sink 510 comprises a copper heat sink located in body 401 of chamber 400 such that excess heat is conducted away from crystal 507. Sensor 511 measures the temperature of holder 508, cooler 509, bridge 510 and crystal 507 such that optimum operating temperatures are maintained. In accordance with this aspect of the present invention, thermal management of crystal 507 is obtained, thereby eliminating the need for coolant liquids which may unnecessarily compromise and complicate the operation of detector 10.

ILS laser system 500 is suitably arranged such that the angle (ϕ) of the beam exciting crystal 507 and the reflected beam from mirror 503 is on the order of about 20° to about 30°, more preferably from about 23° to about 27°, and optimally about 25°. This beam may suitably be directed to the sample system 400A such that detection of contaminants within the system may readily be obtained.

Output beam A from ILS laser 500 after passing through sample system 400A is suitably directed to spectrometer 600. Such direction can be obtained, such as shown in FIG. 2, through use of a folding mirror 601 suitably mounted in a mirror mount 602. Mirror 601 preferably comprises a plane mirror containing a coating for high reflectivity in the desired spectral region (e.g. 1350 nm to 1550 nm). In accordance with a particularly preferred embodiment of the present invention comprises model 5103 available from New Focus of Sunnyvale, Calif.

With continued reference to FIG. 2, spectrometer 600 suitably comprises dispersive gratings designed to spectrally resolve a coherent beam, such as the absorption spectrum of the contaminant in the sample to be detected. Suitably, the spectral dispersion of the spectrometer is sufficiently large to clearly resolve the absorption features of such contaminant, thus enabling the identification of the "signature" of each contaminant and the quantitative determination of the concentration of the contaminant. While any now known or hereafter devised spectrometer may be utilized in accordance with the present invention, preferably spectrometer 600 comprises two diffraction grating assemblies 600A and 600B operating in conjunction with an optical beam expanding assembly 600C and a focusing lens assembly 600D. Optical beam expanding assembly 600C preferably comprises lenses 603 and 605 suitably mounted within detector 10 through use of mounts 604 and 606. Lens 603 preferably comprises a negative lens with an AR coating at between about 1000 nm and 1500 nm, optimally 1400 nm; lens 605 preferably comprises a collimating lens with an AR coating at about 1000 nm and 1500 nm, optimally 1400 nm. In accordance with a particularly preferred aspect of the invention, lens 603 comprises a model KBC013,AR.18 available from Newport of Chicago, Ill. and lens 605 comprises a model KBX115,AR.18 available from Newport of Chicago, Ill.

Diffraction grating assemblies 600A and 600B suitably comprise respective diffraction gratings 607 and 609 mounted on respective diffraction grating mounts 608 and 610. As will be appreciated, mounts 608, 610 permit tuning and adjustment of diffraction gratings 607, 609 within spectrometer 600. In this regard, and in accordance with a preferred aspect of the present invention, mounts 608 and 610 suitably include respective adjustments that enable the efficient and accurate tuning and adjustment of diffractions gratings 607 and 609.

Focussing lens assembly 600D preferably comprises a lens 611 having dimensions on the order of about 50.8 nm by 50.8 nm, containing an AR coating at about 1000 nm and 1500 nm, optimally 1400 nm. Lens 611 is suitably positioned within a lens holder (not shown) which also enables its accurate placement and adjustment within spectrometer 600.

In accordance with a preferred aspect of the present invention and with continued reference to FIG. 2, the spectrally-resolved ILS absorption spectrum produced by spectrometer 600 is suitably displaced spatially across a focal plane located at a fixed distance from lens 611. In accordance with a particularly preferred aspect of the present invention, a multichannel array detector 701 is suitably fixed on a mount 702. An electronic board 703 containing the control and timing electronics required to operate and read information from the multichannel detector 701 is operatively connected to detector 701. Detector 701 is suitably located in the optical beam exiting the spectrometer 600 such that it is sensitive over the region which the ILS laser operates. As a result, the entire spectrally dispersed absorption spectrum of the particular contaminant sought to be identified through use of detector 10 can be obtained. As will be described in greater detail below, the positions and relative intensities of the specific absorption features of the contaminant can be utilized to uniquely identify the detected gas (contaminant) as well as quantitatively determine the amount of the gas (contaminant) so detected.

The light detected by detector 701 is preferably transduced into electronic signals at each detector element (pixel) with signals thereafter transferred to an analog-to-digital (A/D) converter 801 through board 703. Converter 801 is suitably connected through a BNC connector and shielded cable 704 such that the accurate transfer of information is ensured. As will also be described in greater detail below, once the data is so converted, it is manipulated by a computer 802 which may be suitably programmed to convert the electronic signals into spectral information i.e. spectral signatures identifying a particular gas (contaminant) and concentration of gases (contaminants). Detector 701 preferably comprises an InGaAs multichannel (256 pixel 100 μm spacings) array detector. For example, model J18M-FP-100X 5OU:256E from E.G.&G. of Sunnyvale, Calif. or model SU256L-17T-1-100B from Sensors Unlimited of Princeton, N.J. may be advantageously employed in accordance with the present invention.

With reference now to FIGS. 2, as previously mentioned, detector 10 is caused to operate once pumping laser 100 causes ILS laser 500 to operate at or near its threshold level. In cases where the optical characteristics of driver 100 suitably match those of ILS laser 500, no additional modification of the output of driver 100 is necessary. However, in those cases where the remote volume of the pumping radiation of driver 100 does not suitably match the gain medium of ILS laser 500, beam modification system 200 can be utilized to facilitate such matching. In its simplest form, beam modification system 200 preferably comprises an optical telescope useful to optimize the radiation delivered to ILS laser 500 by focusing the required photon density into the correct location and volume of the gain medium of ILS laser 500. Specifically, beam modification system 200 is used to alter the pumping radiation of driver 100 to meet the requirements of laser 500.

In accordance with a particularly preferred aspect of the present invention, beam modification system 200 comprises a beam expanding telescope. Specifically, in such cases where pumping laser 100 comprises the preferred Spectra Physics diode pump and ILS crystal 507 comprises a $Cr^{4+}$:YAG or a $Cr^{4+}$:LuAG crystal, beam expansion of the pumping laser output is necessary.

Figure 4:
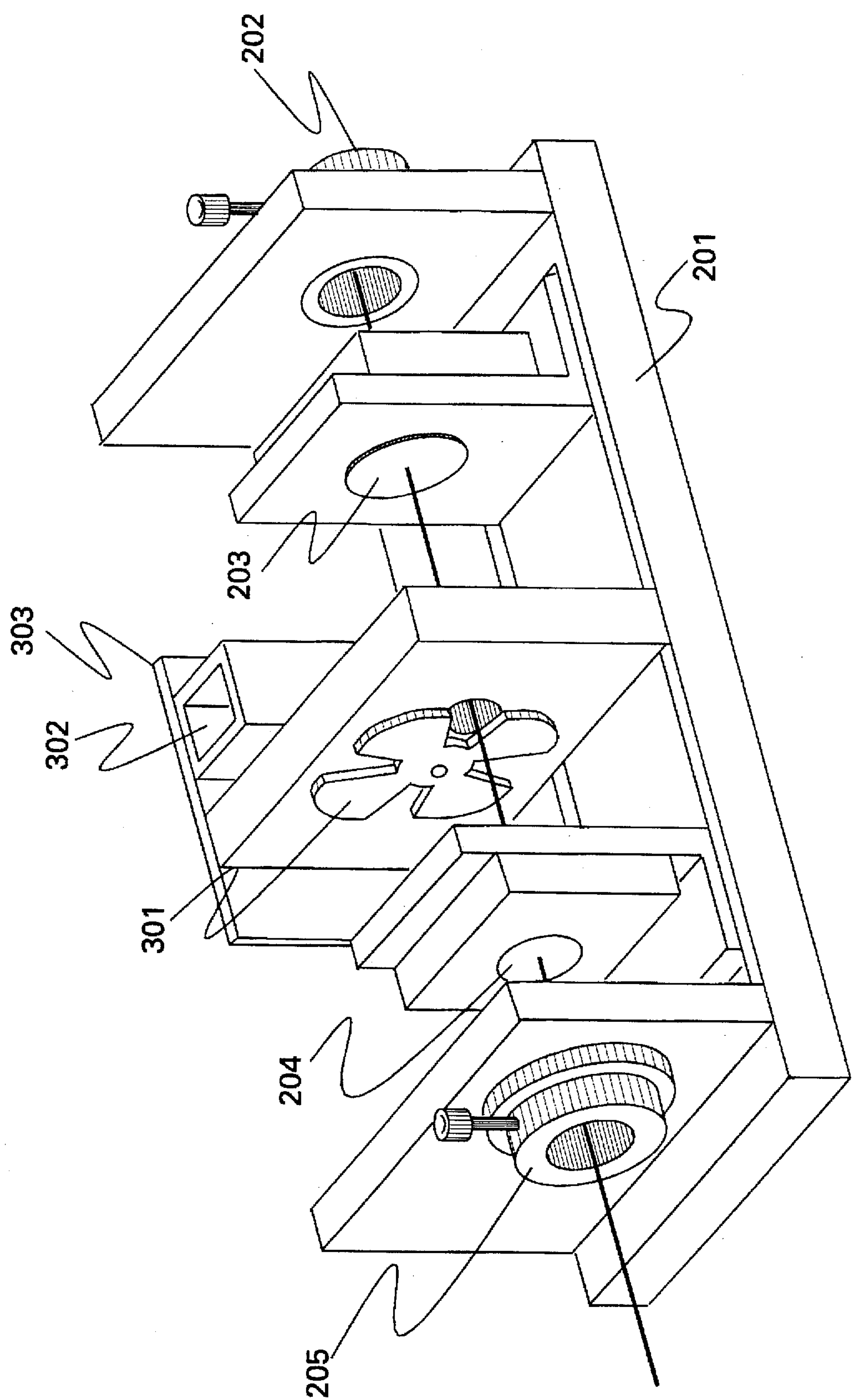
FIG. 4 is an enlarged perspective view of a preferred exemplary embodiment of a beam shaping assembly including a chopper element which may be advantageously used in connection with the contaminant detector system shown in FIG. 2.

As shown best in FIG. 4, system 200 suitably comprises a series of lenses and adjustable apertures. In particular, a frame 201 is provided which suitably includes respective upstanding walls into which respective variable aperture devices 202 and 205 are suitably provided. While any appropriate means of varying the aperture of the opening into which the output (e.g. beam E) of laser 100 enters or exits system 200 may be employed, suitably, devices 202 and 205 comprise conventional aperture varying devices such as model ID-0.5 available from Newport of Chicago, Ill. System 200 also preferably includes a focusing lens 203 and a collimating lens 204. Preferably, lens 203 comprises a focusing lens with an AR coating at about 1000 nm to 1100 nm, optimally about 1064 nm; lens 204 preferably comprises a collimating lens with an AR coating at about 1000 nm to 1100 nm, optimally about 1064 nm. As shown in FIG. 4, lenses 203 and 205 are suitably attached to frame 201 to permit their respective alignment within beam E.

With continued reference to FIG. 2, in some applications, it may be necessary that the incoming beam be appropriately focused into the laser medium (e,g., ion-doped crystal or glass) 507 within ILS laser 500. In accordance with the preferred aspect of the present invention, a focusing lens 206 may be advantageously mounted in a laser lens mount 207 such that lens 206 is suitably located within the path of beam F. In accordance with a particularly preferred aspect of the present invention, focusing lens 206 suitably comprises an optical focusing lens with an AR coating of between about 1000 nm and about 1100 nm and optimally 1064 nm coating. In accordance with this aspect of the present invention, lens 206 is suitably selected such that it has a focal length in the range of about 10 centimeters (cm) and a diameter on the order of about 2.54 cm. Focusing lens 206 may be suitably configured to evidence a plano-convex or convex-convex configuration. A particularly preferred optical focusing lens comprises model KPX094,AR.18 available from Newport of Chicago, Ill.

As will be appreciated by those skilled in the art, the quality of the quantitative information obtainable through use of detector 10 depends, at least in part, on stable operation of ILS laser 500. In the context of the present invention, the stability of laser 500 depends directly on how reproducibly ILS laser 500 reaches threshold. Desirably, pumping laser 100 suitably pumps ILS laser 500 continuously near threshold where its greatest sensitivity may be obtained. However, not all drivers are capable of reliably operating in a continuous fashion. In addition, operating continuously tends to require substantial effort to maintain amplitude and wavelength stability which may have an adverse impact on cost and thereby produce an adverse impact on the commercial viability of detector 10. As an alternative to operating ILS laser 500 continuously, and in accordance with a preferred embodiment of the present invention, ILS laser 500 is operated in a so-called "chopped mode". As used herein, the term "chopped" mode refers to the process of reproducibly exposing ILS laser 500 to pumping radiation and, then, periodically sampling the output of ILS laser 500 which contains the absorption information. Through operation in a "chopped mode", a stable laser operation consistent with the quantitative spectral and concentration measurements may be obtained in a commercially viable manner. While any now known hereafter devised manner of producing a chopped mode can be utilized in accordance with the present invention, advantageously such mode is obtained through use of modulation assembly 300.

Referring again to FIG. 2, in accordance with a preferred embodiment of the present invention, modulation assembly 300 comprises modulator 301 (provided with appropriate electronic circuitry) and modulator 304 (also provided with appropriate electronic circuitry). Modulator 301 advantageously modulates the intensity of output beam E from pump laser 100 and lens 203, while modulation device 304 suitably modulates the output beam of ILS laser 500 that exits chamber 400, thereby periodically sampling the output of ILS laser 500. Suitably, modulator 301 alternatively blocks pumping beam E from reaching ILS laser 500 gain medium (e.g., crystal 507), while modulator 304 alternatively blocks ILS laser beam exiting chamber 400 from reaching both spectrometer 600 and detector 700. Such intensity modulation (e.g. interruption) can be achieved utilizing, among other things, a mechanically operated chopper, an acousto-optic modulator, a shutter and the like. Alternatively, the output intensity of laser 100 may be modulated instead of secondarily chopping the output beam. Desirably, modulating device 300 does not steer the pumping beam and is synchronized to modulate the intensity of the ILS laser output beam exiting chamber 400.

While specific form and placement of modulation assembly 300 is variable, use of modulation assembly 300 enables generation of a reproducible, effective optical path length within ILS laser 500. Stated another way, by varying the generation time ($t_g$), i.e. the time period over which intracavity mode competition within ILS laser 500 is permitted to occur, the effective absorption path length within the intracavity resonator can be controlled and selected to achieve optimum quantitative application of detector 10.

In accordance with this aspect of the present invention, beam E is periodically prevented from reaching ILS laser 500 by rotating modulator 301 which periodically blocks and transmits the pumping laser beam E. Preferably, modulator 301 comprises a mechanical chopper such as BEM Model 350 available from Boston Electronics of Brookline, Mass. Mechanical chopper 301 is suitably placed so that beam E is modulated before reaching ILS laser 500. While chopper 301 may be advantageously placed before or after beam modification system 200, in accordance with a preferred embodiment of the invention, chopper 301 is suitably placed at the focal point within beam modification system 200. As best illustrated in FIG. 2, chopper 301 is suitably mounted in frame 201 of the beam modification assembly 200.

It should be appreciated that chopper 301 could be replaced by any device, e.g., mechanical or electro-optical, which periodically blocks or modulates the pumping laser beam. As previously mentioned, in accordance with the present invention, the intensity of the pumping radiation emanating from laser 100 must only fall below that required to make ILS laser 500 reach threshold and therefore, is not required to reach a zero value.

Suitably, chopper 301 rotates between an open and closed position. Chopper 301 is suitably driven by a chopper driver 303 (e.g. model 350C available from Boston Electronics of Brookline, Mass.) connected to chopper through use of a suitable electrical connector(s) 302 (e.g. model A9049-ND available from Digikey of Theif River Falls, Minn.). As driver 303 causes chopper 301 to rotate to the open position, beam E reaches ILS laser 500, thereby bringing ILS laser 500 above threshold for laser activity. ILS laser 500 continues to operate until driver 303 causes chopper 301 to rotate to the closed position, whereupon chopper 301 effectively blocks pumping beam E from reaching ILS laser 500. ILS laser 500 output exiting chamber 400 is suitably directed to modulator 304. In accordance with various aspects of the present invention, modulator 304 comprises an acousto-optic modulator, such as model ATM80A1 available from IntraAction of Bellwood, Ill. It should be appreciated, however that other available devices, for example, another mechanically operated chopper or even a shutter may be suitably employed for this purpose. As discussed above, to extract quantitative information from the ILS laser 500 exiting beam, modulator 301 periodically samples the output of ILS laser 500 which contains the absorption data of contaminants (e.g. gaseous species) contained in the particular sample. Suitably modulator 304 samples the output and deflects it to spectrometer 600 and detector 700 for analysis.

Modulating device 301 is advantageously synchronized with modulation device 304 such that quantitative information from ILS laser 500 can be extracted in a time-resolved manner. Pump radiation E is effectively delivered to ILS laser 500 intermittently by passing pump beam E through chopper 301. Delivering radiation intermittently alternatively brings ILS laser 500 near threshold and below threshold. After the generation time, $t_g$, elapses as ILS laser 500 nears its threshold, ILS laser 500 output is deflected by modulator 304 to the entrance of spectrometer 600 and detector 500 for detection. However, ILS laser 500 output beam G is deflected to spectrometer 600 and detector 500 for only a short time interval determined by the synchronization of modulation devices 301 and 304. The synchronization of modulators 301 and 304 ensures that radiation from ILS laser 500 is sampled over a well-defined time interval ($t_g$).

Synchronization of modulators 301 and 304 may be achieved by several conventional methods such as, for example, through electronic control by a digital circuit (not shown) operated by computer 802 operatively connected to detector 10. Typically, synchronization of modulators 301 and 304 will be suitable to generate generation times ($t_g$) on the order of less than about 300–500 μsec, more preferably on the order of less than about 10–100 μsec, and optimally on the order of less than about 1 μsec. Such synchronization results in chopper 301 being open at a time when modulator 304 is closed and the time interval between when modulator 301 open and modulator 304 opens determined by $t_g$.

In accordance with a preferred embodiment of the present invention, a method for detecting the presence and concentration of contaminants in a gas utilizing detector system 10 suitably comprises reducing gases (contaminants) in sample system 400A to an acceptable level, placing a sample of gas to be detected in sample system 400A, pumping ILS laser 500 at or near threshold, periodically sampling the optical output from ILS laser 500, preferably via modulation assembly 300, measuring the absorption spectrum of the gases (contaminants) within the sample with spectrometer 600 and detection system 700, and analyzing the absorption spectrum to identify the gaseous species (contaminants) and determine its concentration within the sample utilizing computer/software system 800.

More particularly, reducing gases (contaminants) in chamber 400 (excluding sample system 400A) to an acceptable level may suitably comprise purging or evacuating sealable container 401 with top 410 such that the level of gases (contaminants) is below that to be detected in the gas sample within system 400A. As discussed previously, other mechanisms for reducing the level of gases (contaminants) may be utilized provided they can reduce the level to an acceptable level. Preferably, container base 401 is sealed to top 410 and contaminants contained therein are effectively removed (or reduced to an acceptable level). Desirably, base 401 and top 410 are effectively sealed prior to delivery to a user in a relatively tamper-proof manner.

A sample is suitably communicated to system 400A by connecting a gas line to connectors 408, 409 and feeding the gas into sample system 400A (for example, when the sample comprises a corrosive gas), or into the chamber itself (for example, when the sample comprises a non-corrosive gas).

Pumping ILS laser 500 at or near threshold more particularly comprises selecting the correct pump laser 100 power, focusing conditions at laser crystal 507 utilizing beam modification optics 200 and lens 206, and modulation conditions utilizing modulator system 300. The method for detecting gaseous species in accordance with the present invention further comprises driving ILS laser 500 at or near threshold. In accordance with the present invention, driver 100 suitably pumps ILS laser 500. Where necessary, pumping beam E is suitably shaped by beam shaping assembly 200 to meet the optical requirements of ILS laser 500. Further, where detector 10 is operated in a chopped mode, as described above, modulation assembly, and in particular, modulator 301 periodically interrupts pump beam E thereby preventing beam E from reaching ILS laser 500. Beam F output from modulator 301 and beam shaping assembly 200 is suitably directed to ILS laser 500.

In accordance with this method, as beam F enters chamber 400 through window 402 disposed in the wall of sealed container body 401, beam F is suitably directed to ILS laser 500. Additional focusing and direction of beam F may suitably be achieved as beam F passes from window 402 to focusing lens 206, where focusing lens 206 suitably focuses beam F and directs it through mirror 501. Beam F suitably pumps crystal 507 at or near threshold, and the output beam is suitably directed to the gas sample within system 400A, such as by mirrors 503 and 505. The exiting beam, containing the absorption data from the gas (contaminant) sample, then exits gas chamber 400 through window 403 suitably disposed in a wall of sealed container body 401.

Preferably, where ILS laser 500 is operated in a chopped mode, modulator 304, suitably synchronized to modulator 301, periodically samples ILS laser 500 output beam and passes the sample thus obtained to spectrometer 600 and detector 700. Suitably, mirror 601 directs sampled ILS laser 500 output beam G to spectrometer 600 and detector 700.

The method for detecting gaseous species in accordance with the present invention further comprises analyzing the sampled ILS laser 500 output beam G. Preferably, spectrometer 600 spectrally resolves and detector 700 suitably analyzes sampled ILS laser 500 beam G. Spectrometer 600 suitably spectrally disperses ILS laser 500 beam G through beam expanding assembly 600C, diffraction assemblies 600A, 600B and focusing assembly 600D. Spectrally-resolved ILS absorption data exiting spectrometer 600 is suitably displaced spatially to be detected by multichannel detector 701.

Figure 6:
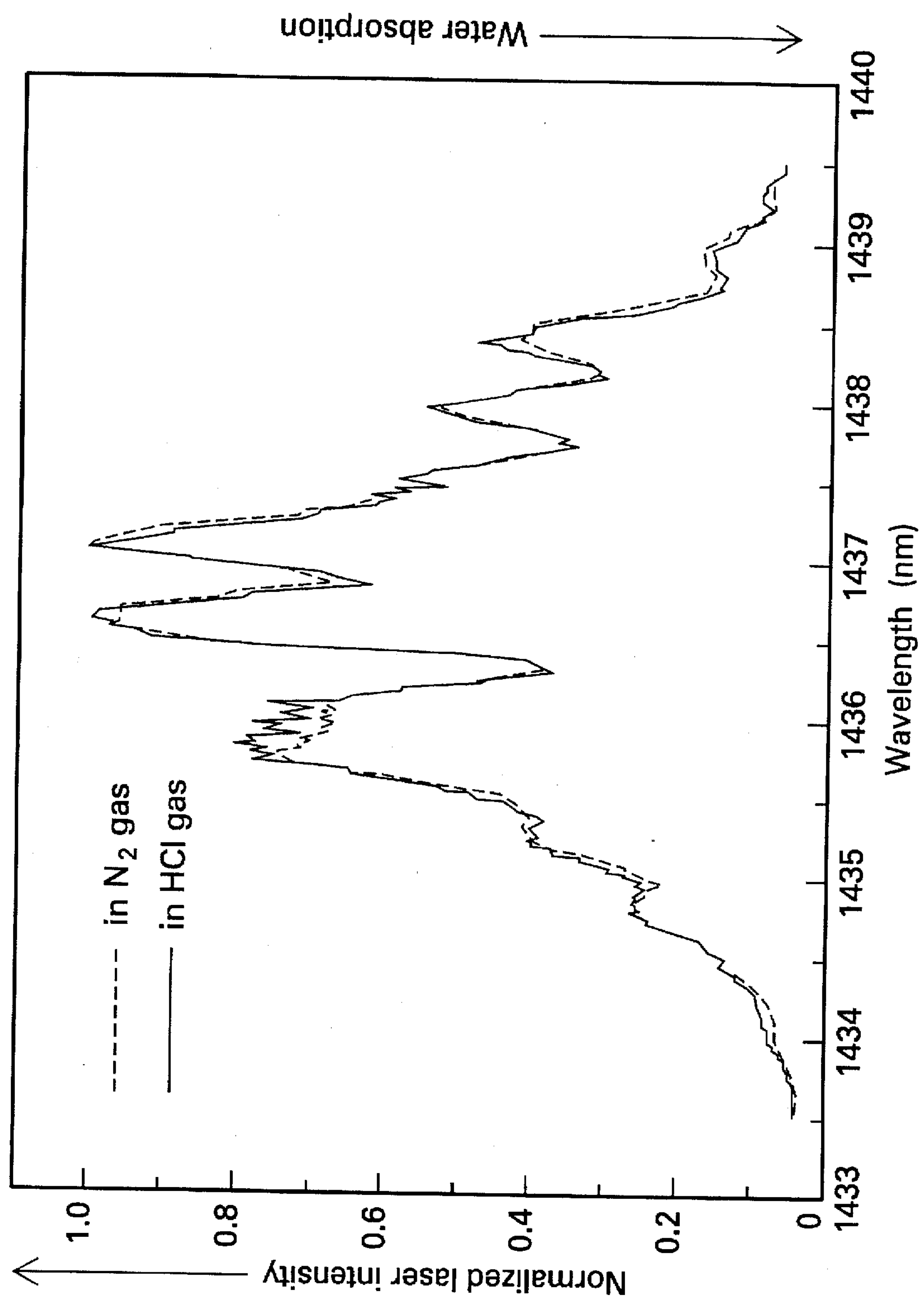
FIG. 6 is a graph showing an exemplary water absorption spectrum in $N_2$ and HCI gases over the wavelengths of 1433–1440 nm.
Figure 7:
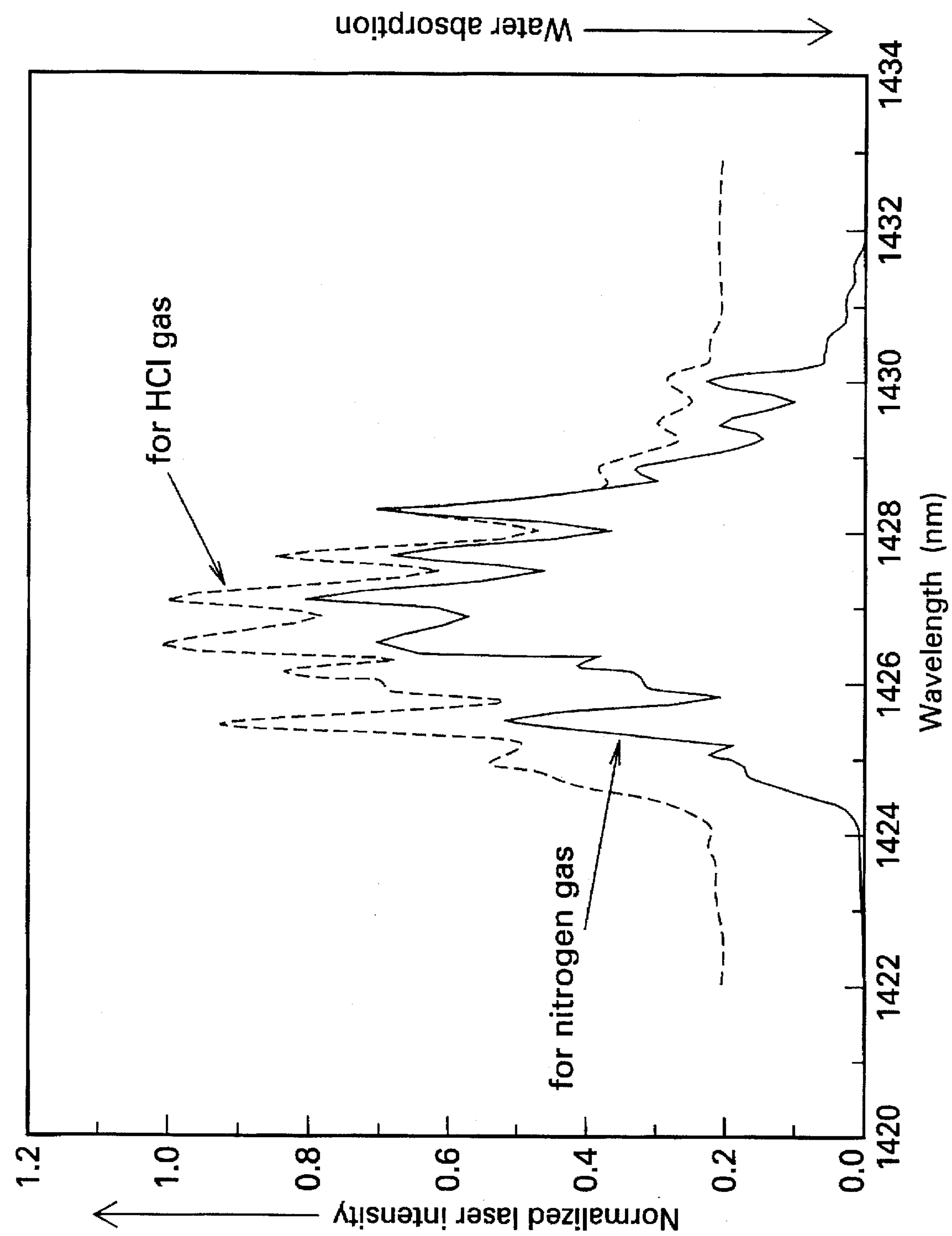
FIG. 7 is an ILS water absorption in $N_2$ and HCI gases over the wavelengths of 1420–1431 nm.

With reference now to FIGS. 6 and 7, detector 10 can be utilized to obtain absorption spectrum for contaminants, such as water vapor, in corrosive (e.g. HCl) or non-corrosive (e.g. $N_2$) over a variety of wavelength regions. As shown in FIG. 6, showing a plot of normalized laser intensity/absorption vs. wavelength over the region of about 1433 nm to about 1440 nm, and in FIG. 7, showing a similar plot over the wavelength region of about 1420 nm to about 1434 nm, signatures of a water vapor in each environment can be obtained through operation of detector 10. The spectrum displayed in FIGS. 6 and 7 were obtained by scanning of spectrometer assembly 600 under control of computer 802 and measurement of the output of diode 701. As will be appreciated, each data point illustrated results from a variety of measurements.

Figure 8:
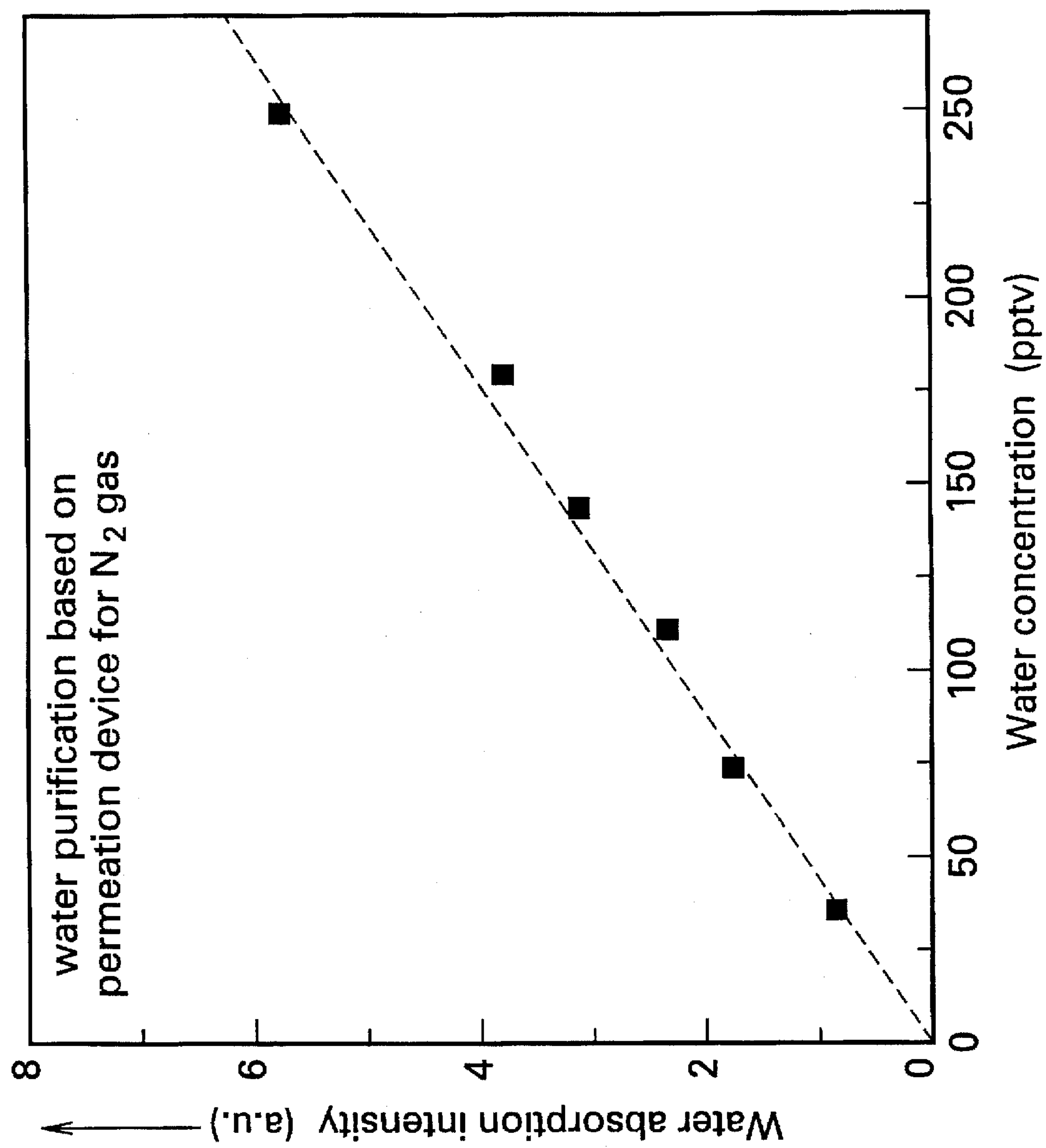
FIG. 8 is a graph showing water absorption intensity versus water concentration as determined by permeation tube/volume expansion techniques.
Figure 9:
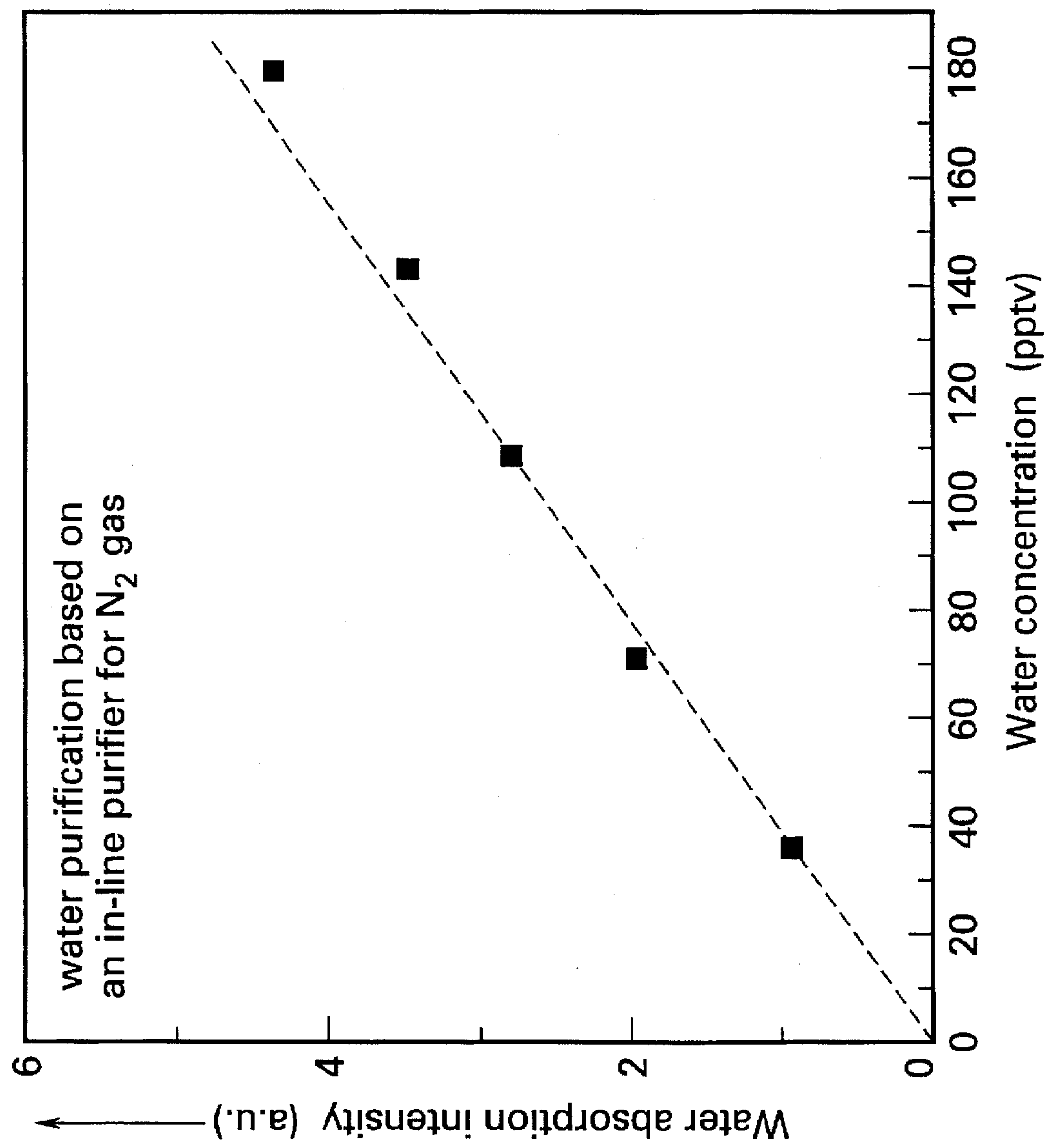
FIG. 9 is a graphical depiction of water absorption intensity versus water concentration also in the 1420–1430 nm region as determined by an in-line purifier.

Given the relationship between intensity and concentration, once a characteristic signature of the contaminant gas, e.g. water vapor, is obtained, the concentration of the contaminant contained within the sample can be readily obtained. While in accordance with the present invention computer 802 is suitably programmed to interpret the data and provide an output indicative of the presence and/or concentration of the contaminant contained within the sample, representative plots as obtained through operation of detector 10 showing the high sensitivity detector possible through use of the present invention illustratively shown in FIG. 8 and 9. In FIG. 8, detector 10 is used as a permeation device; in FIG. 9, detector 10 is used as an in-line purifier.

Those skilled in the art will appreciate that the detection levels available through practice of the present invention generally exceed those which are obtainable through use of conventional devices. Moreover, detector 10 can be used in-line and obtain ready, near real-time measurement of the presence and amount of the contaminant contained in a specific sample, thus addressing the many disadvantages associated with the use of such conventional devices.

It should be understood that the foregoing description relates to preferred exemplary embodiments of the invention, and that the invention is not limited to the specific forms shown herein. Various modifications may be made in the design and arrangement of the elements set forth herein without departing from the scope of the invention as expressed in the appended claims. Moreover, the application of detector 10 as well as the location of detector 10 in, for example a semiconductor fabrication assembly, can vary as may be desired. For example, the specific placement of the various elements within the ILS chamber and detector 10 itself may be modified so long as their configuration and placement suitably enables optical excitation of ILS laser 500 in a readily reproducible manner. These and other modifications in the design, arrangement and application of the present invention as now known or hereafter devised by those skilled in the art are contemplated by the amended claims.

I claim:

1. A detection system for detecting the presence of a contaminant in a sample, comprising:

a chamber suitably configured to be evacuated of contaminants to be detected in the sample, said chamber including therewithin an intracavity laser comprising a laser crystal contained within an intracavity resonator, and a sample system for containing the sample suitably placed within an astigmatically compensated region of said resonator;

a spectrometer assembly; and a detector assembly suitably connected to a computer system programmable to interpret the spectral resolution of said spectrometer assembly and provide an output indicative of the presence and/or concentration of contaminant in the sample.

2. The detection system of claim 1 including a driver having an output that pumps said laser crystal.

3. The detection system of claim 2 including beam shaping optics located outside said laser cavity that shapes said output of said driver.

4. A method for detecting contaminants contained within a gaseous sample comprising the steps of:

directing the output beam of a driver to a laser crystal contained within an intracavity resonator contained within an evacuable/purgable chamber to excite said laser crystal near a threshold level;

providing a sealed sample system for containing the sample to be detected in an astigmatically compensated region of the intracavity resonator in which said laser crystal is maintained;

directing the output energy from said laser crystal to said sample;

resolving the spectral absorption of said laser output after interaction with said sample to determine the presence of and/or amount of any contaminants which may be contained within the sample.

5. The method of claim 4 wherein said output beam of said driver is chopped.

6. The method of claim 4 wherein said output energy from said laser crystal after interacting with said sample is directed to a detector assembly for determining the presence of and/or amount of said contaminants.

7. The method of claim 6 wherein said output energy from said laser crystal after interacting with said sample is alternately prevented from reaching said detector assembly.

* * * * *